United States Patent
Carney et al.

(10) Patent No.: US 7,888,304 B2
(45) Date of Patent: Feb. 15, 2011

(54) USE OF CARRAGEENAN IN AN ENZYME FLUSH

(75) Inventors: Sara A. Carney, De Pere, WI (US); David William Koenig, Menasha, WI (US); Junaid Begawala, Skokie, IL (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 366 days.

(21) Appl. No.: 11/831,552

(22) Filed: Jul. 31, 2007

(65) Prior Publication Data
US 2009/0036341 A1    Feb. 5, 2009

(51) Int. Cl.
*C11D 3/00* (2006.01)
*C11D 7/42* (2006.01)
*C11D 3/28* (2006.01)
*C12S 9/00* (2006.01)

(52) U.S. Cl. .................. 510/392; 510/119; 510/123; 510/126; 510/128; 510/130; 510/136; 510/137; 510/138; 510/141; 510/155; 510/156; 510/158; 510/159; 510/160; 510/161; 510/393; 510/433; 510/501; 560/160; 514/54; 426/335; 426/532; 426/656; 426/658; 604/159; 604/163; 604/171; 604/267

(58) Field of Classification Search .................. 510/392, 510/393, 123, 119, 126, 128, 130, 136, 137, 510/138, 141, 155, 156, 158, 159, 433, 501; 560/160; 514/54; 426/335, 532, 656, 658; 604/159, 163, 164, 170, 171, 267

See application file for complete search history.

(56) References Cited

U.S. PATENT DOCUMENTS

| | | | |
|---|---|---|---|
| 4,138,292 A * | 2/1979 | Chibata et al. ............. 435/178 |
| 4,452,892 A | 6/1984 | Rosevear | |
| 4,894,056 A | 1/1990 | Bommarito | |
| 5,424,299 A | 6/1995 | Monte | |
| 5,880,076 A * | 3/1999 | Vermeer ...................... 510/123 |
| 6,241,996 B1 * | 6/2001 | Hahn .......................... 424/439 |
| 6,258,771 B1 * | 7/2001 | Hsu et al. ................... 510/418 |
| 6,369,018 B1 * | 4/2002 | Hsu et al. ................... 510/418 |
| 6,592,926 B2 * | 7/2003 | Ong et al. ................... 426/575 |
| 2003/0040454 A1 | 2/2003 | Cuperus et al. | |

FOREIGN PATENT DOCUMENTS

| | | |
|---|---|---|
| EP | 0038603 A2 | 10/1981 |
| EP | 0056111 A1 | 7/1982 |
| EP | 0065376 A1 | 11/1982 |
| JP | 2007044156 | 2/2007 |

OTHER PUBLICATIONS

Sabadini, et al., "The Effects of Sucrose on the Mechanical Properties of Acid Milk Proteins-k-Carrageenan Gels," Brazilian Journal of Chemical Engineering, vol. 223, No. 1, pp. 55-65 (Jan.-Mar. 2006).
Borgault, et al., "Prophylactic Pancreatic Enzyme to Reduce Feeding Tube Occlusions," Nutrition in Clinical Practices, vol. 18, pp. 398-401 (Oct. 2003).
International Search Report and Written Opinion for PCT/IB2008/052883 mailed Mar. 24, 2009.

* cited by examiner

*Primary Examiner* — Gregory R Del Cotto
*Assistant Examiner* — Preeti Kumar
(74) *Attorney, Agent, or Firm* — Armstrong Teasdale LLP

(57) ABSTRACT

The present disclosure is directed to methods and compositions for clearing and cleaning enteral feeding tubes. More particularly, the composition is an ingestible gel composition that comprises enzymes for degrading buildup in enteral feeding tubes, carrageenan, and divalent metal ions or a source thereof. The carrageenan present in the composition stabilizes the enzymes at room temperatures, allowing for long-term storage of the composition. Upon injecting the gelled composition into the feeding tube, body heat from the patient melts the gel, and the enzymes are released to act on debris present in the feeding tube.

17 Claims, No Drawings

USE OF CARRAGEENAN IN AN ENZYME FLUSH

BACKGROUND OF DISCLOSURE

The present disclosure is generally directed to methods and compositions for clearing and cleaning enteral feeding tubes. More particularly, the composition is an ingestible gel composition that comprises enzymes for degrading buildup in enteral feeding tubes, carrageenan, and divalent metal ions or a source thereof. The carrageenan present in the composition stabilizes the enzymes at room temperatures, allowing for long-term storage of the composition. Upon injecting the gelled composition into the feeding tube, body heat from the patient melts the gel, and the enzymes are released to act on debris present in the lumen of the feeding tube.

Many acutely and chronically ill patients cannot properly chew or swallow their food or medication, and as a result may become severely malnourished. Consequently, food and/or medication must be delivered to the patient in a different manner. Gastroenterologic feeding tubes have been known for years and have been used to provide nutrition and medication to patients who are unwilling or unable to obtain nutrition by swallowing.

Feeding tubes may be inserted into the stomach (gastrostomy tubes) or intestines (jejunostomy tubes) by any one of a number of different methods. Generally, a catheter is placed in the body by way of the mouth and is pulled or pushed downward into the stomach and either left there or is pushed further down into the jejunum of the small intestine. The feeding tubes may also enter the body either by way of the nasal passageway, or through open surgical, endoscopic, laproscopic, or radiologic techniques. For example, a feeding tube may be surgically implanted through the abdomen. The most common type of feeding tube is a percutanenous endoscopic gastronomy (PEG) tube, which is inserted into the patient endoscopically.

During the use of enteral feeding tubes, residual food, proteins, starches, cellulose, and/or medication may accumulate in and block the feeding tube. Occlusions in general can be caused by inappropriate administration of medications, poor flushing techniques, thick formulas, or reflux of gastric or intestinal contents up into the tube. In addition to preventing food composition from passing through the tube to the stomach, such blockages also provide a ready site for the growth and multiplication of bacteria. It is therefore important to regularly clean the feeding tube to prevent such blockages.

A variety of means are known for cleaning enteral feeding tubes. For example, U.S. Pat. No. 4,894,056 describes a method and device for restoring the patency of feeding tubes that involves contacting occlusions in the tubes with a combination of solubilizing agents and mechanical force. Other techniques may involve the use of pressurized fluids or suction to flush the tube. However, these techniques may be time consuming, run the risk of rupturing the tube if high pressure is used, and may involve removal and reinsertion of the tube, causing discomfort to the patient.

Enzyme solutions have also been used to maintain or restore feeding tube patency. However, while enzymes themselves may be an effective means of preventing or dissolving blockages in feeding tubes, there are drawbacks to the use of enzymes solutions. For instance, many biological materials, such as enzymes, are known to have a limited shelf life. This is generally considered to be a result of enzyme instability at storage temperature, e.g., at room temperature. The shelf life of certain enzymes may be extended by storing them at refrigeration temperatures, but even under refrigeration, relatively short shelf lives are common.

As will be appreciated, biologically active proteins, such as enzymes, are generally folded in a complex three dimensional manner which is unique to each protein. The ultimate structure of an enzyme may be affected by a number of environmental factors; for example, temperature, pH, the presence or absence of certain co-factors or metals, the presence of oxygen, oxidizing or reducing agents, and the presence of water or moisture. Where conditions are not optimal, an enzyme may not form properly or may denature such that its biological function is lost or is at least diminished.

Enzyme flushes are normally made in solution. However, water may hydrolyze the enzymes present in the flush solution in a time and temperature dependent manner, resulting in denaturation and potential loss of enzyme function. One way to maintain enzyme stability over extended periods of time is to incorporate chemical inhibitors into the flush solution, which may act to hold the enzymes in the solution inactive until use. However, since the flush solution used to clean enteral feeding tubes will ultimately end up being ingested by the patient, it is often not desirable to incorporate chemical inhibitors into the solution. Furthermore, dehydrating enzyme solutions may not improve their stability, as during dehydration and at the high temperatures at which known dehydration procedures may occur, the proteins may also be denatured.

There is thus a need for an enteral feeding tube cleaning composition which has an extended shelf life, and can also be safely ingested by a patient.

SUMMARY OF THE DISCLOSURE

The present disclosure is generally directed to methods and compositions for clearing and cleaning enteral feeding tubes. More particularly, the composition is an ingestible gel composition that comprises enzymes for degrading buildup in enteral feeding tubes, carrageenan, and divalent metal ions or a source thereof. The carrageenan present in the composition stabilizes the enzymes at room temperatures, allowing for long-term storage of the composition. Upon injecting the gelled composition into the feeding tube, body heat from the patient melts the gel, and the enzymes are released to act on debris present in the lumen of the feeding tube.

In one aspect, the present disclosure is directed to a method of clearing and cleaning the lumen of a feeding tube, the method comprising injecting an ingestible gel composition into the feeding tube, the ingestible gel composition comprising carrageenan, a divalent metal ion or source thereof, and an enzyme for degrading buildup in the tube, wherein the composition has a viscosity of at least about 9,000 centipoise at room temperature, and a viscosity of about 4,000 or less at body temperature.

In another aspect, the present disclosure is directed to a method of clearing and cleaning the lumen of a feeding tube, the method comprising injecting an ingestible composition into the feeding tube, the ingestible gel composition comprising from about 0.5% (w/v) to about 2.0% (w/v) of iota carrageenan, from about 0.01% (w/v) to about 1.0% (w/v) of a divalent metal ion or source thereof, and from about 5% (w/v) to about 60% (w/v) of an enzyme for degrading buildup in the tube.

Other objects and features will be in part apparent and in part pointed out hereinafter.

DETAILED DESCRIPTION OF THE DISCLOSURE

The present disclosure is generally directed to methods and compositions for clearing and cleaning enteral feeding tubes. More particularly, the composition is an ingestible gel composition that comprises enzymes for degrading buildup in enteral feeding tubes, carrageenan, and divalent metal ions or a source thereof. The carrageenan present in the composition stabilizes the enzymes at room temperatures, allowing for long-term storage of the composition. Upon injecting the gelled composition into the feeding tube, body heat from the patient melts the gel, and the enzymes are released to act on debris present in the lumen of the feeding tube.

It has been discovered that incorporating certain amounts of carrageenan and divalent metal ions into an enzyme flush composition produces a composition having unique properties and improved shelf-life. Specifically, the method of the present disclosure uses ingestible gel compositions comprising an enzyme for degrading buildup in feeding tubes, carrageenan, and a divalent metal ion or source thereof to clear buildup or blockages of food, medication, or other debris that may be present in the lumen of feeding tubes. Unlike prior flush compositions, the present composition advantageously is a gel at room temperature. Without wishing to be bound to any particular theory, it is believed that the carrageenan present in the composition, in combination with the divalent metal ion, forms a three-dimensional matrix at room temperature, entrapping the enzymes and water present in the composition within the matrix. The thixotropic properties of the carrageenan allows the composition to be injected into the feeding tube in a gel form, where body heat from the patient warms the gel. As the gel composition is warmed, the carrageenan network begins to melt and break down, releasing the bound enzymes and water. The resulting viscous composition slowly drains down the feeding tube, degrading buildup and removing occlusions present in the tube.

The methods of the present disclosure have several advantages over previously known flush compositions. For instance, the carrageenan network present in the ingestible gel composition is capable of suspending particulates, such as the enzymes, relatively uniformly over extended periods of time. Advantageously, the carrageenan network also binds up water present in the composition. By separating the enzymes and the water within the carrageenan network, the water activity in the gel composition is reduced, improving the stability of the enzymes. As a result, the gel composition may be stored at room temperatures for extended periods of time while maintaining enzyme stability. Advantageously, the enzyme stability is achieved without the need for chemical stabilizers, which may otherwise adversely affect the ingestibility of the composition. As such, the compositions of the present disclosure may safely be ingested Additionally, the ingestible gel compositions of the present disclosure advantageously are formulated so that they will melt at around body temperature. After the gel composition is injected into the feeding tube, heat from the patient's body begins to melt the gel composition, resulting in breakdown of the carrageenan network. This in turn causes the enzymes and water bound up in the network to be released, forming a viscous liquid composition comprising active enzymes. The viscosity of the composition at body temperature is preferably such that the composition will drain down the feeding tube. The viscous nature of the composition advantageously allows the composition to better adhere to the internal surfaces of the feeding tube, increasing the contact time between the enzymes and any buildup present in the tube, and improving composition efficacy.

As noted above, the ingestible gel compositions of the present disclosure advantageously comprise carrageenan. Carrageenans are a naturally occurring family of carbohydrates, extracted from red seaweed. Specifically, carrageenans are linear sulfated polysaccharides made up of repeating galactose units and 3,6-anhydrogalactose joined by alternating α 1-3 and β 1-4 glycosidic linkages. There are three main types of carrageenan: lambda carrageenan, kappa carrageenan, and iota carrageenan. The types of carrageenan differ based on the number and position of the ester sulfate groups on the repeating galactose units. In the presence of cations, iota and kappa carrageenan polymers align themselves to form individual helices, which can further associate with the cations to form a gel matrix.

For purposes of the present invention, it is generally preferred that the ingestible gel composition comprise iota carrageenan. Iota carrageenan has the following structural formula:

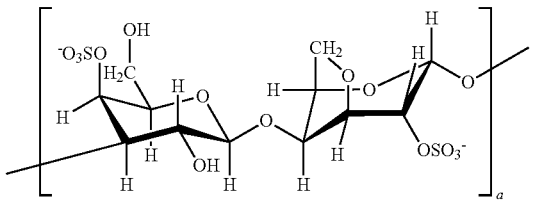

wherein a is any number greater than 10, and preferably is greater than 100. Preferably, the molecular weight of the iota carrageenan is about 100,000 or greater.

Iota carrageenan forms a durable, elastic gel in the presence of certain divalent cations. Advantageously, iota carrageenan is also thixotropic. Because of the thixotropic nature of the iota carrageenan, the viscosity of the gel composition is reduced when the composition is subject to shear, such as when it is injected into the feed tube. This allows the gel composition to be injected into the feed tube while still in a viscous, gel-like state.

Although iota carrageen is generally preferred, in certain embodiments, the compositions of the present disclosure may comprise a combination of iota carrageenan, kappa carrageenan, and lambda carrageenan. Preferably, however, at least about 65% of the carrageenan in the composition will be iota carrageenan.

As noted above, the carrageenan present in the composition may be gelled by interaction with cations present in the composition. The type of cation used to gel the composition will typically vary depending on the type of carrageenan used. Typically, when the carrageenan is iota carrageenan, the cation is a divalent metal ion, such as calcium, magnesium, beryllium, strontium, barium, and combinations thereof. Preferably, the divalent metal ion is calcium.

In certain embodiments, the compositions may comprise a source of a divalent metal ion, such as a divalent salt. Exemplary divalent salts include calcium chloride ($CaCl_2$), calcium fluoride ($CaF_2$), calcium bromide ($CaBr_2$), calcium iodide ($CaI_2$), magnesium chloride ($MgCl_2$), magnesium fluoride ($MgF_2$), magnesium bromide ($MgBr_2$), magnesium iodide ($MgI_2$), strontium chloride ($SrCl_2$), strontium fluoride ($SrF_2$), strontium bromide ($SrBr_2$), strontium iodide ($SrI_2$), beryllium chloride ($BeCl_2$), beryllium fluoride ($BeF_2$), beryllium bromide (BeBr$_2$), beryllium iodide (BeI$_2$), barium chloride (BaCl$_2$), barium fluoride (BaF$_2$), barium bromide (BaBr$_2$), and barium iodide (BaI$_2$), among others. Preferably, the divalent salt is selected from the group consisting of calcium chloride, calcium fluoride, calcium bromide, calcium iodide, and combinations thereof. More preferably, the divalent salt is calcium chloride. The divalent salt may be hydrated, or alternately, may be in anhydrous form.

The physical properties of the ingestible gel compositions of the present disclosure may be controlled by varying the type and concentration of carrageenan present in the composition, as well as the type and concentration of cation present in the composition. In particular, it has been discovered that the composition may be formulated so that it is a gel at room temperature (e.g., from about 15° C. to about 25° C.), but becomes a liquid, and preferably a viscous liquid, when warmed to body temperature (e.g., about 37° C.).

For instance, the compositions of the present disclosure will preferably have a viscosity of at least about 6000 cps, more preferably at least about 7000 cps, and still more preferably at least about 9000 cps at room temperature, and a viscosity of about 4000 cps or less, more preferably about 2000 cps or less, and still more preferably about 1000 cps or less at body temperature. Preferably, the composition has a viscosity of at least about 9000 cps at room temperature, and a viscosity of about 4000 cps or less at body temperature. As is known in the art, viscosity can be readily determined by conventional methods and viscometers such as a Brookfield viscometer, and the like.

As noted above, the viscosity of the composition used in the methods disclosed herein should be selected such that the composition is a gel at room temperature. In particular, the properties of the composition at room temperature should be such that the three-dimensional carrageenan network is maintained, and the enzymes and water present in the composition remain entrapped in the network and separated from each other. If the composition is not gelled at room temperature, e.g., the viscosity of the composition is too low, the carrageenan network will not maintain the separation of the enzymes and water present in the composition, resulting in increased water activity in the composition and reduced enzyme stability.

Furthermore, the composition should have a viscosity at body temperature low enough to allow the composition to drain down the feeding tube. If the viscosity of the composition is too high at body temperature, the composition will not be able to drain down the feeding tube. Furthermore, the enzymes and water will remain trapped within the carrageenan network, and the enzymes will not be free to act on debris present in the lumen of the tube. It is generally advantageous, however, for the composition to be slightly viscous at body temperature. The slightly viscous nature of the composition at body temperature will reduce the speed at which the composition drains down the feeding tube, therefore increasing the contact time between the enzymes and the lumen of the feeding tube, improving composition efficacy.

As noted above, the properties of the composition may vary depending on the concentration of the carrageenan in the composition and the concentration of the divalent metal ion in the composition. In general, as the ion concentration increases, the temperature at which the composition gels will increase, and the temperature at which the gelled composition melts will also increase. Furthermore, increasing the cation concentration in the composition also typically increases the strength of the gel. The mechanical properties of the gel may be measured using any suitable technique, such as described in Sabadini, et al., Brazilian J. of Chem. Eng., Vol. 223, No. 1, pp. 55-65 (January-March 2006), herein incorporated by reference.

For purposes of the present disclosure, the concentration of carrageenan present in the compositions is typically from about 0.5% (w/v) to about 2.0% (w/v), more preferably from about 0.75% (w/v) to about 1.5% (w/v), and more preferably is about 1.0% (w/v).

Typically, the divalent metal ion or source thereof is present in the composition at a concentration of about 0.01% (w/v) to about 1.0% (w/v), more preferably is present in the composition at a concentration of about 0.01% (w/v) to about 0.02% (w/v), and more preferably at a concentration of about 0.015% (w/v). In one preferred embodiment, the composition comprises from about 0.5% (w/v) to about 2.0% (w/v) carrageenan and about 0.01% (w/v) to about 1.0% (w/v) divalent metal ion or source thereof. Preferably, the composition comprises about 1.0% (w/v) iota carrageenan and about 0.015% (w/v) calcium ion or source thereof.

The compositions of the present disclosure also comprise at least one enzyme that can be used to degrade buildup present in the lumen of a feeding tube. As noted above, enteral feeding tubes are frequently occluded by food and other medications. The ingestible gel compositions of the present disclosure may be used both prophylactically to prevent occlusions from forming in the tube, as well as to restore tube patency after occlusion buildup. In particular, the enzymes may act to facilitating the hydrolysis or degradation of food proteins, starches, celluloses, lipids, and the like.

Preferably, the enzymes used in the compositions of the present disclosure are ingestible and have been given a generally regarded as safe (GRAS) status by the U.S. Food and Drug Administration. It is also generally preferable that the enzyme have maximum or near maximum enzymatic activity at between about 31° C. to about 44° C., and preferably at about 37° C., and at a pH of from about 4 to about 6.

Preferably, the enzyme is selected from the group consisting of proteases, lipases, cellulases, amylases, and combinations thereof. Examples of suitable proteases include serine proteases, cysteine proteases, metalloproteases, threonine proteases, aspartic acid proteases, and glutamic acid proteases. Specific examples of serine proteases include subtilisin serine proteases such as proteinase K and chymotrypsin-like serine proteases such as chymotrypsin, trypsin, and elastase. Specific examples of cysteine proteases include papain, cathepsins, caspases, and calpain proteases. Examples of other suitable proteases include keritinases and collagenases. In one preferred embodiment, the enzyme may be a papain, such as from *Carica papaya*. In another preferred embodiment, the enzyme may be a lipase such as from *Candida cylindracea*. In another embodiment, the enzyme may be a cellulase such as from *Trichoderma longibrachiatum*. In one preferred embodiment, the composition comprises a combination of papain, lipase, and/or cellulase.

The compositions typically comprise from about 5% to about 60% (w/v), and more preferably from about 20% to about 40% (w/v) of enzyme. In one particular embodiment, when the enzyme is papain, the papain may be present in the composition in an amount of from about 20% to about 60% (w/v) at 600,000 USP trypsin units (TU)/g, and preferably about 40% (w/v) at 600,000 TU/g. In another embodiment, when the enzyme is lipase, the lipase may be present in the composition in an amount of from about 20% to about 60% (w/v) at 200,000 FIP/g, and preferably about 40% (w/v) at 200,000 FIP/g. In still another embodiment, when the enzyme is cellulase, the cellulase may be present in composition in an amount of from about 10% to about 30% (w/v) at 150,000 cellulase units (CU)/g, and preferably about 20% (w/v) at 150,000 CU/g.

In addition to the enzymes, carrageenan, and divalent metal ion or source thereof, the compositions of the present disclosure may further comprise water. Typically, the composition comprises from about 5% (w/v) to about 40% (w/v) water, and preferably from about 10% (w/v) to about 20% (w/v) water.

Additionally, the compositions of the present disclosure may also optionally comprise a thickener. Inclusion of a thickener into the composition may help increase the viscosity of the composition, even after the composition has melted upon injection into the feeding tube. As discussed above, having a more viscous composition helps the composition adhere to the internal surfaces of the feeding tube, increasing contact between the enzymes and any build up present in the tube and improving composition efficacy.

Examples of suitable thickeners include alginate, xanthan, pectin, arabinoxylan, cyclodextrins, locust bean gum, pullulan, dextran, inulin, and combinations thereof. The thickeners are typically included in the compositions in amounts of from about 0.01% (w/v) to about 1.0% (w/v), and more typically about 0.5% (w/v).

In certain embodiments, an enzyme flush composition may be prepared that comprises enzymes, a thickener, as described above, optionally a divalent metal ion or source thereof, but no carrageenan. In this embodiment, the composition would not be a gel at room temperature, but rather, would be injected into the feeding tube as a viscous liquid. As noted above, the viscosity of the liquid will help the composition adhere to the internal surfaces of the feeding tube and to residual food and debris attached thereto. In these embodiments, the viscosity of the composition is typically from about 100 cps to about 300 cps, and preferably is about 250 cps.

Typically, the compositions of the present disclosure will have a pH of from about 3 to about 7, and more preferably from about 5 to about 6.

The ingestible gel compositions of the present disclosure are preferably administered by injection into the feeding tube. In particular, the ingestible gel composition of the present disclosure can be readily injected into the feeding tube using any injection means, including, but not limited to, needles, syringes, and the like. The amount of composition injected into the tube is not critical, but is preferably sufficient to clean or clear debris buildup from the lumen of the feeding tube.

The compositions of the present disclosure may be made by any suitable means, such as described in the Examples. Typically, the composition components are dispersed in cold water with stirring. The mixture is then gradually heated to a temperature above the solublility temperature of the carrageenan, and typically to about 60° C. to about 80° C., while stirring. Once all composition components have been dissolved, the mixture is allowed to gel as it cools to room temperature. Optionally, the composition may be drawn into a syringe or other suitable injection means while still in the liquid phase, and allowed to cool within the injection device. In this embodiment, the composition gels within the injection means and is ready for injection into the feeding tube once cooled.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

Preparation of a Carrageenan-Containing Flush Composition

In this example, an ingestible gel composition comprising carrageenan was prepared. The composition was prepared by slowly dissolving 2% (w/v) iota carrageenan in 200 mL of RO water on a hot plate heated to 80° C. Once the iota carrageenan was dissolved, the mixture was cooled to 45° C., and an equal volume of $CaCl_2$ and bovine serum albumin (BSA) was added to the mixture at a concentration of 0.03% (w/v) $CaCl_2$ and 0.5% (w/v) BSA. The composition was allowed to cool to room temperature and to gel. The resulting gel composition comprised 1% (w/v) iota carrageenan, 0.015% (w/v) $Ca^{2+}$, and 0.25% (w/v) bovine serum albumin (BSA).

Example 2

Effect of Varying Carrageenan and Calcium Ion Concentrations on Gelling Profile

In this example, the effect of different concentrations of carrageenan and calcium ion on the properties of carrageenan-containing flush compositions was determined.

The compositions tested in this example comprised iota carrageenan and calcium chloride monohydrate at varying concentrations, and 0.25% (w/v) of bovine serum albumin (BSA). The concentration of carrageenan ranged from 0.2% to 2% (w/v), and the concentration of calcium chloride monohydrate ranged from 0.01% to 1% (w/v). Specific concentrations of iota carrageenan and calcium chloride monohydrate are set forth in Table 1.

To prepare the compositions, mixtures of iota carrageenan, calcium chloride monohydrate, and 0.25% (w/v) BSA were added to 200 mL of RO water on a hot plate. The mixtures were slowly dissolved, as the solution was heated to 80° C., stirring rapidly. Once all components were dissolved, the mixture was allowed to cool to room temperature. As the mixture cooled, the properties of the composition were observed. The results are set forth in Table 1.

TABLE 1

| Carrageenan (% w/v) | $CaCl_2 \cdot 2H_2O$ (% w/v) | Observations |
|---|---|---|
| 1.25% | 0.1% | Was gelled at around 65° C. Gel is durable and had no observable stress fractures |
| 1.25%* | 0.01% | Was gelled at around 55° C. |
| 1.0% | 0.2% | Gelling had already begun at 70° C. Not a strong gel at 40° C. Poor consistency Very viscous; appeared to absorb water |
| 1.0% | 0.05% | Was gelled at around 55° C. |
| 1.0% | 0.01% | Slightly viscous at 37° C. More gel-like at 30° C. Viscous but not yet gelled at 25° C. |

TABLE 1-continued

| Carrageenan (% w/v) | CaCl$_2$•2H$_2$O (% w/v) | Observations |
|---|---|---|
| 1.0% | 0.02% | Viscous but still flowing at 37° C. |
|  |  | Was gelled at 30° C. |
| 1.0% | 0.015% | Fluid at 37° C. |
|  |  | Viscous but not a gel at 30° C. |
|  |  | Was gelled at 22° C. |

*In this example, the carrageenan was added to the RO water and dissolved prior to addition of the BSA and calcium chloride monohydrate.

As can be seen from these results, the physical properties of the carrageenan-containing compositions can be varied depending on the Ca$^{2+}$ and carrageenan concentration. In this example, compositions comprising 1.0% (w/v) carrageenan and either 0.02% (w/v) or 0.015% (w/v) calcium chloride monohydrate were gels at room temperature, but fluid or a viscous fluid at body temperature (37° C.).

Example 3

Preparation of an Alginate-containing Flush Composition

In this example, an ingestible gel composition comprising alginate, but no carrageenan was prepared. To begin, a mixture of sodium alginate, papain, lipase, and cellulase was prepared by vortexing the enzymes and alginate together to form a homogenous powder. The powder mixture was dumped into a falcon tube containing 35 mL of RO water, and the tube was capped and shaken using a pattern of 3-5 vigorous shakes, followed by one minute of sitting, until the powder was dissolved. The resulting composition comprised 0.2% (w/v) papain, 0.2% (w/v) lipase, 0.1% (w/v) cellulase, and 0.5% (w/v) sodium alginate and had a pH of 7.2 and a viscosity of 195 cps.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and methods without departing from the scope of the disclosure, it is intended that all matter contained in the above description shall be interpreted as illustrative and not in a limiting sense.

What is claimed is:

1. A method of clearing and cleaning the lumen of a feeding tube, the method comprising injecting an ingestible gel composition into the feeding tube, the ingestible gel composition comprising iota carrageenan, a divalent metal ion or source thereof, and from about 20% (w/v) to about 40% (w/v) of an enzyme for degrading buildup in the tube, wherein the composition has a viscosity of at least about 9,000 centipoise at room temperature, and a viscosity of about 4,000 or less at body temperature.

2. The method of claim 1 wherein the composition comprises from about 0.5% (w/v) to about 2.0% (w/v) carrageenan.

3. The method of claim 1 wherein the divalent metal ion is selected from the group consisting of calcium, magnesium, beryllium, strontium, barium, and combinations thereof.

4. The method of claim 3 wherein the divalent metal ion is a calcium ion.

5. The method of claim 1 wherein the composition comprises from about 0.01% (w/v) to about 1.0% (w/v) of the divalent metal ion.

6. The method of claim 1 wherein the enzyme is selected from the group consisting of protease, lipase, cellulase, amylase, and combinations thereof.

7. The method of claim 1 wherein the enzyme is selected from the group consisting of papain, lipase, cellulase, and combinations thereof.

8. The method of claim 7 wherein the composition comprises about 40% (w/v) of papain at 600,000 TU/g.

9. The method of claim 7 wherein the composition comprises about 40% (w/v) of lipase at 200,000 FIP/g.

10. The method of claim 7 wherein the composition comprises about 20% (w/v) of cellulase at 150,000 CU/g.

11. The method of claim 1 wherein the enzymes degrade protein, starch, cellulose, lipids, and combinations thereof present in the lumen of the tube.

12. The method of claim 1 wherein the composition further comprises from about 5% (w/v) to about 40% (w/v) water.

13. The method of claim 1 wherein the composition has a pH of from about 3 to about 7.

14. A method of clearing and cleaning the lumen of a feeding tube, the method comprising injecting an ingestible gel composition into the feeding tube, the ingestible gel composition comprising from about 0.5% (w/v) to about 2.0% (w/v) of iota carrageenan, from about 0.01% (w/v) to about 1.0% (w/v) of a divalent metal ion or source thereof, and from about from about 20% (w/v) to about 40% (w/v) of an enzyme for degrading buildup in the tube.

15. The method of claim 14 wherein the composition has a viscosity of at least about 9,000 centipoise at room temperature, and a viscosity of about 4,000 or less at body temperature.

16. The method of claim 15 wherein the divalent metal ion is a calcium ion.

17. The method of claim 16 wherein the composition comprises about 0.015% (w/v) of calcium ion and about 1.0% (w/v) iota carrageenan.

\* \* \* \* \*